United States Patent [19]

Banik

[11] Patent Number: 4,689,229
[45] Date of Patent: Aug. 25, 1987

[54] GASTROINTESTINAL COMPOSITIONS

[76] Inventor: Upendra Banik, 4435 King Street, Pierrefonds Quebec, Canada, H9H 2G2

[21] Appl. No.: 759,280

[22] Filed: Jul. 26, 1985

[30] Foreign Application Priority Data

Aug. 10, 1984 [CA] Canada .................................. 460794

[51] Int. Cl.$^4$ .................... A61K 35/78; A61K 31/715
[52] U.S. Cl. .................................. 424/195.1; 514/57; 514/925; 514/926
[58] Field of Search ..................... 424/195.1; 514/925, 514/926, 57

[56] References Cited

U.S. PATENT DOCUMENTS 3,973,051  8/1976  Buckley et al. ..................... 426/574
3,982,003  9/1976  Mitchell et al. ........................ 426/1

OTHER PUBLICATIONS

Handbook of Nonprescription Drugs 6th ed., 1979, p. 48.
H. D. Fein—Modern Drug Encyclopedia and AA—Therapeutic Index (1961) Robt. Donnelley Corpo, p. 1135 "Siblin".

Primary Examiner—Johnnie R. Brown
Assistant Examiner—John W. Rollins
Attorney, Agent, or Firm—Omri M. Behr

[57] ABSTRACT

Gastrointestinal compositions containing from 99 to 70 percent by weight of plantago and from 1 to 30 percent by weight of pectin, useful for inhibiting the occurrence of gastroduodenal ulcers and for preventing their recurrence, for reducing the incidence and severity of undesirable side effects caused by anti-ulcer drugs, and for alleviating discomfort occasioned by gastroesophageal reflux. Methods for their preparation and use are also disclosed.

10 Claims, No Drawings

GASTROINTESTINAL COMPOSITIONS

BACKGROUND OF THE INVENTION (a) Field of Invention

The present invention relates to gastrointestinal compositions containing mixtures of plantago and of pectin, to a process for preparing said compositions and to the use thereof for the inhibition and/or prevention and/or alleviation of certain gastrointestinal disorders. More specifically, the gastrointestinal compositions of this invention are useful for inhibiting the occurrence of gastroduodenal ulcers and for alleviating certain symptoms of gastrointestinal distress associated with gastritis or with the presence of such ulcers. In particular, they are surprisingly useful in preventing the recurrence of gastroduodenal ulcers following the discontinuation of therapy with anti-ulcer drugs, and for reducing the incidence and severity of undesirable side effects of said anti-ulcer drugs. Moreover, they are also useful in alleviating discomfort caused by gastroesophageal reflux and for regularizing bowel movements in constipated as well as in diarrheal patients, with concomitant relief from discomfort and pain. The gastrointestinal compositions are particularly distinguished by the absence of undesirable side effects.

(b) Prior Art

Statistics Canada, Causes of Death, Vital Statistics, Vol. IV, Statistics Canada, Health Division, 1984, pp. 96–99 reported that 16,352 people died in Canada from gastrointestinal diseases in 1982. It is not known how many people in Canada are suffering each year from gastroduodenal ulcers. It is estimated that gastroduodenal ulcers (peptic ulcers) affect between 5% and 6% of adults in the U.S.A. with approximately 300,000 new cases diagnosed each year, Jadhav, G. R. et al: Drug Therap., p. 183, Jan 1983. Total digestive disorders afflict nearly 20 million Americans, at an estimated annual cost of over 8 billion dollars in medical expenses alone, National Commission on Digestive Diseases, Vol. I. U.S. Dept. of Health, Education and Welfare. Public Health Service, NIH, DHEW, Publication No. NIH: 79-1878, Jan. 1979, p. 1. In some countries it is believed that almost 20% of individuals may suffer from peptic ulceration during their lifetime, D. W. Piper, Book Reviews, Practitioner 227:529, 1983. Various factors such as stress, diet, some drugs, alcohol, smoking, inheritence factors etc. seem to be responsible for causing peptic ulcers. The importance of the problem, both from the point of view of public health as well as from that of the national economy, is undoubtedly of a very high order.

In view of the common belief that gastroduodenal ulcers were mainly caused by excess production of digestive acids, research for an effective ulcer therapy has traditionally focussed upon inhibiting those acids, although it is now known that many patients suffering from gastroduodenal ulcers secrete amounts of acid which are within, or even below, normal physiological values, (see e.g. A. L. Blum et al., Pt. II, Acta Hepato-Gastroenterol. 22, 123, 1975 and J. Rhodes, Gastroenterology 63, 171, 1972). Attempts to strengthen the ability of the gastroduodenal mucosa to resist those acids seem to have been largely neglected, although one of the fathers of modern physiology, Claude Bernard (1813–1878) had already pointed out the importance of that resistance when he stated that " . . . the epithelium of the gastric mucosa, especially the glutinous mucus which covers the inner wall, thus encloses the gastric juices as in a vase, as impermeable as though it were made of porcelain . . . " (cited by P. E. O'Brien, Clin. Surg. Int. 7, Chapter 3, p. 28, D. C. Carter, Ed. Churchill Livingstone, Edinburgh London Melbourne and New York 1983). However, several types of anti-ulcer agents such as H2-receptor antagonists, (e.g. cimetidine, ranitidine), coating agents (e.g. sucralfate, tripotassium di-citrato-bismuthate), certain anti-inflammatory agents (e.g. carbenoxolone), and antacids appear to be effective in healing gastric and/or duodenal ulcers when administered at recommended doses, and certain cytoprotective agents such as prostaglandins E-2 and I-2 would appear to be promising are presently under study. However, all of those agents exhibit certain undesirable side effects which are not shown by the gastrointestinal compositions of this invention, and which will be discussed below.

The histamine $H_2$-receptor antagonists cimetidine and ranitidine are potent systemic anti-ulcer drugs which have to be administered in fairly high doses for several weeks in order to show significant rates of healing of gastroduodenal ulcers. However, it is now well known that those drugs cannot keep the ulcers healed unless long term therapy is used (see e.g. A. E. Read, Practitioner 227, 535, 1983) and the manufacturers of ranitidine, conscious of the dangers and the disadvantages of prolonged administration of the drug, are recommending that endoscopic examination should be carried out after two weeks of medication " . . . to spare many patients an additional period of treatment . . . " (see Physician's Desk Reference (PDR) 1984, p. 985). Evidence is now accumulating that patients with chronic duodenal ulcers will have to be treated with histamine H2-receptor antagonists for many years, and possibly permanently (G. C. Clark, Practitioner 227, 543, 1983). For those reasons many physicians are now reassessing the value of those drugs, as they are seriously concerned about the concept of permanent treatment of a generally benign disease with potent drugs (see G. C. Clark, cited above). A number of undesirable side effects have also been observed and have been summarized by G. L. Kauffman, Jr. in J. Clin. Gastroenterol. 3 (Suppl. 2), 95, 1981; they include diarrhea, muscular pain, dizziness, rash, mild gynecomastia, mental confusion, lethargy, restlessness, disorientation, agitation, hallucination, twitching, and apnea. In addition, ranitidine is also stated to cause a significant incidence of headache, as well as occasional malaise, constipation, nausea, and abdominal pain, see PDR 1984 p. 985 cited above. However, it would appear that the most serious disadvantage of the histamine H2-receptor antagonists is the fact that gastroduodenal ulcers which had healed under treatment with those drugs frequently recur after cessation of medication. G. R. Jadhav et al., cited above, reported that the rate of recurrence was 42 percent to 70 percent three months after discontinuation of cimetidine therapy, and 74 percent to 90 percent after one year, and H. P. Roth, Gastroenterology 61, 570, 1971 reported that 42 percent of ulcer patients experienced recurrence of ulcers within six months. The manufacturers of cimetidine recommend administration of reduced doses of the drug (400 mg at bedtime only instead of 300 mg four times per day) as a prophylactic regimen against the recurrence of ulcers (see PDR 1983, pp. 1912 and 1913), but such a regimen would hardly seem to be conducive to the avoidance of undesirable side effects.

Prostaglandins E-2 and I-2 are believed to be of significant importance in maintaining gastric mucosal integrity and thus to act as cytoprotective agents. Robert et al., Gastroenterology 77, 433, 1979 have also reported that several analogues thereof appear to be effective in preventing gastric mucosal injury induced by a variety of agents, and Konturek et al., Gut 22, 283, 1981 have shown that administration of Prostaglandins E-2 and I-2 prevents gastric mucosal damage induced by aspirin. Those compounds are currently undergoing clinical evaluation for the treatment of peptic ulcers, but it is well known that they cause a number of undesirable side effects among which diarrhea, nausea, and vomiting are the most serious.

Among the systemic anti-inflammatory drugs presently available only carbenoxolone would appear to act locally on the stomach, possibly by stimulant actions upon mucin production and the enzyme processes involved in cellular regeneration, see Martindale Extra Pharmacopoeia 27th edition, 1977, p. 299. G. L. Kauffman, Jr. cited above has reported that carbenoxolone appears to increase the life span of epithelial cells; that it alters the carbohydrate composition of gastric mucus: topical application of carbenoxolone to the stomach lining of rats increased the thickness of the mucous layer by 80 percent; that it may affect the permeability of the gastric mucosa to hydrogen ions; and that it inhibits peptic activity in the gastric luminal fluid without inhibiting gastric acid secretion; that it is effective in the treatment of gastric ulcers, and that it has beneficial effects in cases of duodenal ulcers; that a comparison of the effects of cimetidine and of carbenoxolone upon gastric ulcers had shown 78 percent healing following cimetidine treatment as against 52 percent with carbenoxolone; that the rate of recurrence of gastric ulcers following discontinuation of carbenoxolone treatment was about 40 to 50 percent, and that administration of maintenance doses of carbenoxolone was capable of reducing the recurrence rate from 46 percent to 25 percent; and that administration of maintenance doses of carbenoxolone reduced the rate of recurrence of duodenal ulcers to 21 percent and was thus more effective than the maintenance regimen using cimetidine in patients previously treated with cimetidine in which the recurrence rate was found to be 48 percent. However, carbenoxolone exhibits a number of undesirable side effects of which sodium and water retention with ensuing edema and weight gain, alkalosis, hypertension, and hypokalemia appear to be the most serious and are reported to occur in about 25 to 30 percent of patients, see Martindale, and also G. L. Kauffman, Jr., both cited above. In view of the seriousness of the above side effects a maintenance regimen using carbenoxolone may possible reduce their incidence and severity, but it may hardly be expected to eliminate them altogether.

As an example of a coating agent sucralfate, a sucrosepolysulfate aluminum complex, inhibits pepsin activity in gastric juice and has been shown in vitro to absorb bile salts; it is only minimally absorbed from the gastrointestinal tract and the small amounts which are absorbed are excreted primarily in the urine; it forms an ulcer-adherent complex with the proteinaceous exudate at the site of the ulcer, and experiments in vitro have demonstrated that a sucralfate-albumin film provides a barrier to the diffusion of hydrogen ions (see PDR 1984, pp. 1164-1165). Sucralfate is an effective non-systemic agent for the therapy of duodenal ulcers (D. Hallander, Int. Cong. Gastroenterol. 1982, No. 2205, p. 548) and of gastric ulcers (M. E. Denyer, Practitioner 227, 633, 1983), but although the ulcers may heal after a few weeks of treatment there is no permanent cure: Denyer, cited above, has shown that the rate of recurrence in patients observed 9-12 months after discontinuation of sucralfate medication is about the same as that following treatment with cimetidine, viz., about 70 percent in both groups after one year. However, patients which had been initially treated with sucralfate showed a significantly longer mean of duration of remission (7.3 months) than those initially treated with cimetidine (4.6 months), see Inpharma Aug. 27, 1983, pp. 17-18. The most frequently occurring undesirable side effect of sucralfate medication was constipation reported by 2.2 percent of all patients, with diarrhea, nausea, gastric discomfort, indigestion, dry mouth, rash, pruritus, back pain, dizziness, sleepiness, and vertigo being reported occasionally, see PDR 1984, cited above. Xerostomia, skin eruptions, and abdominal pain associated with acute dosing of sucralfate have also been reported, see Inpharma, Recent Reviews, Sept. 18, 1982, and Sherman et al., Am. J. Gastroenterol. 78, 210, 1983 have reported that sucralfate lowers phosphate levels, probably by phosphate binding in the intestines, and that the drug would appear to be another factor predisposing the ulcer patient to hypophosphatemia and its attendant complications.

Tripotassium di-citrato bismuthate (TDB), a colloidal bismuth preparation also called bismuth subcitrate, is another example of a coating agent. It is believed to possess "ulcer-insulating" and anti-pepsin activities, see T. R. Wilson, Postgrad. Med. J. 51(Suppl. 5), 18, 1975. Van Trappen et al., Gut 21, 329, 1980 have reported that it is more effective than placebo in healing duodenal ulcers, and that it is as effective as cimetidine or slightly superior in that respect. Similar results have also been obtained by Tanner et al., Med. J. Aust. 1, 1, 1979 in patients suffering from gastric ulcers. Concerning the recurrence of ulcers, G. L. Kauffman, Jr., cited above, reported the results of a limited study which showed that the rate of recurrence was higher in patients initially treated with cimetidine than in those initially treated with TDB. Undesirable side effects include blackening of the stool (which may be confused with melena), and sometimes also darkening of the tongue. Furthermore, TDB has an ammoniacal odour which patients may find to be objectionable.

A wide variety of antacids are commonly available, most of them containing aluminum hydroxide, magnesium oxide or hydroxide or trisilicate, or calcium carbonate, or mixtures thereof. Some of them are effective in reducing pain and discomfort associated with gastroduodenal ulcers, and all of them are designed to raise gastric pH levels. Howwever, repeated dosing at short intervals with some of those antacids, a practice which is often resorted to by patients which are not under surveillance, may result in gastric pH levels which exceed the safe limits and which may lead to acid rebound and thus cause additional damage. Antacids containing aluminum hydroxide may cause constipation, and those containing magnesium compounds may cause diarrhea. Furthermore, alkalosis and/or hyper-aluminum, hyper-magnesium, or hyper-calcium states may be observed in patients suffering from renal impairment, see G. L. Kauffman, Jr., cited above.

The above review of the Prior Art shows that the systemic anti-ulcer drugs presently used in the treatment of gastroduodenal ulcers cause a considerable incidence of undesirable side effects, and that even the coating agents and the antacids are not free from causing certain adverse reactions. M. E. Denyer, cited above, has said that " . . . in peptic ulcer therapy, the 1970's could be described as the decade of the acid inhibitors. Perhaps the pendulum is now swinging back and the 1980's will prove to be the decade of the mucosal protective agents . . . ". The present invention is directed towards the latter aim, as will be shown below.

SUMMARY DESCRIPTION OF THE INVENTION

The gastrointestinal compositions of this invention are mixtures containing from 99 to 70 percent by weight of plantago and from 1 to 30 percent by weight of pectin. Preferred compositions contain from 95 to 80 percent by weight of plantago and from 5 to 20 percent by weight of pectin. They are conveniently prepared from commercially available plantago seeds by separating the kernels from the thin, white, translucent membrane in which they are encased and which is usually called the husk, most conveniently by grinding and sieving. The husks which are thus obtained substantially free from the dark red kernels in the form of a colourless powder are then treated with ethylene oxide at 10°–35° C. for 6–12 hours in order to reduce bacterial contamination to an acceptably low level. The husks thus obtained are then either roasted at 120°–180° C. for 0.5 to 2 hours, cooled, and mixed with the appropriate amounts of pharmaceutical grade pectin; or the husks obtained as above are mixed with the appropriate amounts of pharmaceutical grade pectin and the mixture thus obtained is roasted at 120°–180° C. for 0.5 to 2 hours; in both cases the roasting procedure results in a further reduction of bacterial contamination. The cooled mixture thus obtained is ground to the desired degree of fineness and may either be dispensed in bulk, or in unit dosage form as capsules or in individual moisture-resistant sealed pouches, or it may be formed into tablets with the addition of the usual excipients in small amounts, such as disintegrating, lubricating, binding, or colouring agents. Flavouring materials may also be added to any of the above forms of the gastrointestinal compositions of this invention.

Although both plantago and pectin have been known to possess valuable pharmaceutical properties and have been used to treat certain disorders of the digestive system, with the principal use of plantago being that of a bulk-forming laxative and that of pectin as an anti-diarrheal agent, it has now been found, surprisingly, that certain combinations of plantago and of pectin as exemplified in the gastrointestinal compositions of this invention inhibit the occurrence of gastroduodenal ulcers in patients presenting with symptoms indicative of ultimate ulcer formation, and that such gastrointestinal compositions prevent the recurrence of gastroduodenal ulcers in patients in which said ulcers had previously been healed. It has also been found that the gastrointestinal compositions of this invention are useful in alleviating the pain and distress associated with gastritis or with the presence of gastroduodenal ulcers, that they are useful in regularizing bowel movements in diarrheal or in constipated patients, and that they are useful in alleviating the discomfort occasioned by gastroesphageal reflux. Furthermore, it has been found that the gastrointestinal compositions of this invention are useful as adjuncts to certain anti-ulcer agents, in permitting important reductions in the daily dosages of the latter agents and thus diminishing the incidence and severity of undesirable side effects caused by said agents. It is a particular advantage of the gastrointestinal compositions of this invention that they exert their beneficial effects without causing any undesirable side effects. The only side effect observed is the fact that their administration causes a feeling of fullness or satiety, an effect which is greatly appreciated by overweight patients.

The mechanism by which the gastrointestinal compositions of this invention exert their beneficial effects is not precisely known, but it may reasonably be assumed that they exert certain protective effects upon the gastric and duodenal mucosa. They are hydrophilic muciloids which swell in the gastrointestinal tract to form a viscous gel which may possibly adhere to sensitive areas of the gastric and duodenal mucosa and form a barrier against hydrogen ions, certain digestive enzymes such as pepsin, and bile. Because of their hydrophilic nature it is important that the gastrointestinal compositions of this invention be administered together with sufficient fluids to exert maximal beneficial effects, e.g. with at least 250 mL of water for each dose of 1–3 g of the respective composition.

It is an object of this invention to provide gastrointestinal compositions inhibiting the occurrence of gastroduodenal ulcers in patients presenting with symptoms indicative of ultimate ulcer formation.

It is another object of this invention to provide gastrointestinal compositions preventing the recurrence of gastroduodenal ulcers in patients in which said ulcers had previously been healed.

It is a further object of this invention to provide gastrointestinal compositions useful in alleviating pain and distress in patients suffering from gastritis or from gastroduodenal ulcers.

It is another object of this invention to provide gastrointestinal compositions useful in regularizing bowel movements in diarrheal as well as in constipated patients.

It is still another object of this invention to provide gastrointestinal compositions which are useful as adjuncts in the therapy with anti-ulcer drugs by reducing the incidence and severity of undesireable side effects of such anti-ulcer drugs.

These and other objects of this invention and the advantages offered thereby will be apparent from the following description.

Plantago seed has been used as a bulk-forming laxative for such a long time that it has almost become a part of folk medicine. Each seed is encased in a thin, white, translucent membrane or husk which is odorless and tasteless and contains a colloidal polysaccharide mucilage which, upon hydrolysis, yields mainly xylose, arabinose, and galacturonic acid together with minor amounts of rhamnose and galactose. The husks are hydrophilic and absorb as much as twenty times their own weight of water, and swell to form a viscous gel which is indigestible and non-absorbable but which may bind bile salts and cholesterol, see AMA Drug Evaluations, 5th Edition, Chicago, 1983, p. 1302. In addition, it has been found that plantago husks or the viscous gel obtained therefrom after contacting them with water may also bind free hydrogen ions. The seeds of at least two species of Plantago are commercially available (*P. psyllium*, and *P. ovata*), and for the purposes of this invention it is preferred to use the husks obtained from seeds of *P. ovata*. The husks are referred to as plantago throughout the description of the present invention, wherein one of the functions of plantago is that of a bulk-forming agent. The known side effects of plantago are minor, viz., flatulence, and occasional loose bowel movements in some patients, while its main effect is that of a low-fibre, bulk-forming laxative.

Pectin is an essentially linear polysaccharide, with D-galacturonic acid as its main constituent. It is a high-fibre carbohydrate which is present in all land plants and has been part of the human diet since the origin of man, and it is generally recognized as a valuable and harmless food additive. Pectin possesses a number of valuable pharmacological activities, with its anti-diarrheal activity being probably the most widely known. M. Winters and C. A. Tompkins, Am. J. Dis. Child. 52, 259, 1936 have devised a formula containing pectin and agar together with dextrin and maltose as nutrients and have used it successfully in treating infants and small children suffering from diarrhea of divers etiology. M. Winters et al., Am. J. Digest. Dis. 6, 12 1939 have also reported experimental studies in a small group of dogs in which gastric ulcers had been induced by massive doses of cinchophen (100 mg/dog/day); addition of pectin (10.8 g/dog/day) to the diet resulted in a reduction of the incidence of the ulcers, and in two dogs established ulcers were found to be healed after pectin had been added to the diet; the authors concluded that pectin may be of value as a prophylactic and curative agent for peptic ulcers. However, those results have apparently never been confirmed by others, and orally administered pectin, as an extension of its anti-diarrheal effect, is known to cause constipation.

It has now been found, surprisingly, that the gastrointestinal compositions of this invention inhibit the occurrence of gastroduodenal ulcers in patients presenting with symptoms indicative of ultimate ulcer formation, i.e. in patients suffering from conditions which, if left untreated, would be expected to develop ultimately into gastroduodenal ulcers in the opinion of an examining physician. Such symptoms include gnawing or burning pains in the upper abdomen, often simply described by the patient as hunger. Those "hunger pains" may be sufficiently violent to prevent the patient from sleeping, and they usually occur when the stomach is empty. If the threatened area is located in the duodenum eating will usually bring relief, but if it is located in the stomach eating will often aggravate the pains. Antacids may bring temporary relief, but administration of an effective dose of a gastrointestinal composition of this invention inhibits the ultimate formation and thus the occurrence of gastroduodenal ulcers in said patients and maintains them free from pain and discomfort without other medication.

Gastroduodenal ulcers will often recur after having been healed by treatment with anti-ulcer drugs and subsequent discontinuation of such treatment, with the rate of recurrence being disquietingly high. It has now been found, equally surprisingly, that administration of an effective dose of a gastrointestinal composition of this invention to patients in which gastroduodenal ulers had previously been healed by treatment with anti-ulcer drugs and in which said treatment had been discontinued prevents the recurrence of such gastroduodenal ulcers and maintains said patients in a satisfactory state of health without other medication. In this connection it may perhaps be of interest to note that A. Rydning et al., Lancet 1982, II, 736, have reported on their attempts to prevent the recurrence of duodenal ulcers in patients in which such ulcers had recently healed, by allocating one group of such patients to a low-fibre diet and the other to a high-fibre diet, both groups for a period of six months. Recurrence of ulcers was observed in 80 percent of the patients on the low-fibre diet and in 45 percent of the patients in the high-fibre group, and the difference was found to be statistically significant. While the intake of fibre in the diet may be so much higher than that provided by an effective dose of the gastrointestinal composition of this invention that a comparison does not seem to be permissible, it should be noted that the gastrointestinal compositions of this invention contain a major proportion of a low-fibre carbohydrate (plantago) and only a minor proportion of a high-fibre carbohydrate (pectin); their contribution to total fibre intake is therefore on the low side, and the results obtained by their administration would seem to be contrary to those reported by Rydning et al. cited above.

The treatment of patients suffering from active gastroduodenal ulcers with anti-ulcer drugs has usually to be continuous for several weeks or even months, and the occurrence of undesirable side effects of those drugs is not uncommon. Such side effects may be so severe that some patients even prefer to discontinue such treatment altogether, and to revert to simple palliative treatment, e.g. with antacids. It has now been found, again surprisingly, that the daily intake of anti-ulcer drugs may by substantially reduced, to one-half or in some cases even to one-third of the recommended dosage,, by administering an effective dose of a gastrointestinal composition of this invention as adjunct therapy. The incidence and severity of undesirable side effects caused by the respective anti-ulcer drug are thus reduced to an extent which is at least equal to, and in some cases greater than, the proportion of reduction of such incidence and severity which might be expected due to the reduction of intake of said anti-ulcer drug, and in some cases it has been found that undesirable side effects were substantially eliminated.

Gastroesophageal reflux, commonly also known as heartburn, is fairly frequently encountered in patients suffering from gastritis or duodenitis, but it is also seen in normal healthy subjects, especially after a large, spicy, or fatty meal. The regurgitation of gastric contents and of bile into the esophagus causes intense discomfort, which is often aggravated when the patient is lying down or bending over. It has now been found, surprisingly, that the discomfort occasioned by gastroesophageal reflux may be alleviated within a few minutes by administration of an effective dose of a gastrointestinal composition of this invention.

It has also been found that administration of an effective dose of a gastrointestinal composition of this invention regularizes bowel movements, both in constipated as well as in diarrheal patients, with concomitant relief from discomfort and pain.

It has furthermore been found that administration of an effective dose of a gastrointestinal composition of this invention will alleviate pain and distress in patients suffering from gastritis or from active gastroduodenal ulcers.

DETAILED DESCRIPTION OF THE INVENTION

The gastrointestinal compositions of this invention are conveniently prepared from commercially available Plantago seeds, e.g. from the seeds of *P. psyllium* or *P. ovata,* with the latter being preferred. The kernels are separated from the husks by repeated grinding and sieving, to obtain the husks substantially free from particles of the kernels as a colourless powder, preferably of 70-mesh particle size. The husks thus obtained are then maintained in an atmosphere of ethylene oxide at 10°-35° C. for 6-12 hours in order to reduce bacterial contamination to acceptably low levels. The ethylene oxide is then removed and the husks thus obtained are tested for bacterial contamination by the method for determining microbial limits described in USP XX, p. 874 ff., more particularly on p. 877. The contaminating microorganisms have been found to be substantially only nonpathogenic bacteria, and a count of 500-10,000 microorganisms per gram of husks, when obtained after four days of incubation, is deemed to constitute an acceptably low level of bacterial contamination. The husks thus obtained with an acceptably low level of bacterial contamination, which are designated as plantago husks or simply as plantago for the purposes of this invention, are then either roasted at 120°-180° C. for 0.5 to 2 hours, preferably at 150° C. for one hour, and cooled to ambient temperature to obtain roasted husks, followed by mixing 100 parts by weight of said roasted husks with 1.01 to 42.8 parts by weight of pharmaceutical grade pectin to obtain the corresponding gastrointestinal composition of this invention containing from 99 to 70 percent by weight of plantago and from 1 to 30 percent by weight of pectin; or 100 parts by weight of plantago husks obtained as described above are mixed with 1.01 to 42.8 parts by weight of pharmaceutical grade pectin and the resulting mixture is roasted at 120°-180° C. for 0.5-2 hours, preferably at 150° C. for one hour, and cooled to ambient temperature to obtain the corresponding gastrointestinal composition of this invention containing from 99 to 70 percent by weight of plantago and from 1 to 30 percent by weight of pectin. In both cases the roasting step of the process results in an additional reduction of bacterial contamination and in an improved taste and consistency of the product. The gastrointestinal compositions obtained by either procedure are then ground to the desired particle size and may be dispensed in bulk or in unit dosage form in individual moisture-resistant sealed pouches containing 1 or 3 g each of the product, or they may be ground to a very fine powder, e.g. in a Ducon Micropulveriser to pass through a No. 27 screen, and filled into soft gelatin capsules containing 500 mg of the product each. They may also be compressed into tablets containing 0.5 or 1.0 g of the product per tablet, with the addition of small amounts of the usual excipients, such as starch or lactose as disintegrating or binding agents, and such as magnesium stearate or stearic acid as lubricating agents. Flavouring materials may optionally be added in small amounts (e.g. 0.1-5.0 mg of flavour per gram of gastrointestinal composition), and pharmaceutically acceptable colours may optionally be added to the tabletting mixture, for example if it should be desired to colour-code tablets containing different percentages of plantago and of pectin. Examples of such formulations are shown in the following table in parts by weight.

| Plantago | 99 | 95 | 90 | 85 | 80 | 75 | 70 |
|---|---|---|---|---|---|---|---|
| Pectin | 1 | 5 | 10 | 15 | 20 | 25 | 30 |

CLINICAL EVALUATION

A total of 22 patients, all volunteers, have received the gastrointestinal compositions of this invention,, with 12 of those patients having been using them solely for the purpose of regularizing bowel movements at doses of 1-3 g one to three times per day. Those patients have not been followed, but it was found opportune to supply constipated patients with compositions containing elevated proportions of plantago and correspondingly lower proportions of pectin, e.g. 95 percent of plantago and 5 percent of pectin, while diarrheal patients received compositions containing high proportions of pectin and correspondingly lower proportions of plantago, e.g. 80 percent of plantago and 20 percent of pectin. The results obtained with the remaining 10 patients are discussed below.

Inhibition of the occurrence of gastroduodenal ulcers was observed in three patients, all males 53-55 years old, presenting with symptoms indicative of ultimate ulcer formation such as gnawing or burning pains in the upper abdomen, or distressing hunger pains which were often severe enough to prevent the patient from sleeping. Two of those patients had been taking antacids for 1-4 years without obtaining satisfactory results. Administration of 1-3 g of the above gastrointestinal compositions containing from 95 to 90 percent of plantago and from 5 to 10 percent of pectin one to four times per day, with one mandatory administration at bedtime, proved to be an effective dose for the inhibition of ultimate ulcer formation and provided relief in all three patients. Those patients have been followed for 3-6 months and are still free from the above pains and distress without taking any other medication.

Prevention of the recurrence of gastroduodenal ulcers was observed in two male patients 43 and 60 years of age, respectively. Both of them had experienced duodenal ulcers which had healed after treatment with cimetidine and ranitidine at some time prior to commencement of treatment with the gastrointestinal composition, and both were at that time beginning to suffer again from distressing symptoms indicative of future ulcer formation. Administration of 1-3 g of the gastrointestinal composition described above containing 95 percent plantago and 5 percent pectin one to four times per day, with one administration scheduled at bedtime, proved to be an effective dose and has maintained both patients free from distressing symptoms for follow-up periods of 3 and 5 months, respectively, without any other medication.

Reduction in the incidence and severity of undesirable side effects of anti-ulcer drugs was observed in two patients, one a male of 67 years and the other a female 65 years old. Both patients had been diagnosed as duodenal ulcer cases and were under treatment with cimetidine at the recommended dosage levels of 300 mg four times per day, and both patients were suffering from some of the undesirable side effects of the drug, viz., muscular pain, abdominal pain and malaise. Administration of 1-3 g of the gastrointestinal composition described above containing 95 percent of plantago and 5 percent of pectin once a day at bedtime proved to be an effective dose which permitted reduction of the daily intake of cimetidine to one-half of the recommended dosage, with concomitant relief from the undesirable side effects of the drug. Both patients have been followed for 2 months and no undesirable side effects of cimetidine have been reported during the follow-up period.

Alleviation of discomfort occasioned by gastroesophageal reflux was observed in three patients, all healthy males 45–55 years old, who had experienced episodes of gastroesophageal reflux, principally after a large, spicy, and fatty meal. Administration of a single dose of 1–3 g of the gastrointestinal composition containing 90 percent of plantago and 10 percent of pectin described above at the time of such an episode or as soon as possible thereafter proved to be an effective dose and alleviated the discomfort occasioned by gastroesophageal reflux, usually within a few minutes. Two of those patients have been followed for 3 and 5 months, respectively, and substantially similar results have been observed during the follow-up period.

I claim:

1. A process for preparing a gastrointestinal composition which consists of the following steps:
   (a) maintaining plantago husks in an atmosphere of ethylene oxide at 10°–35° C. for 6–12 hours, removing the ethylene oxide, and obtaining plantago husks having acceptably low levels of bacterial contamination;
   (b) roasting said last-named husks at 120°–180° C. for 0.5 to 2 hours, cooling said husks to ambient temperature, and obtaining roasted husks;
   (c) mixing 100 parts by weight of said roasted husks with 1.01 to 42.8 parts by weight of pectin, grinding the mixture, and obtaining the corresponding gastrointestinal composition containing from 99 to 70 percent by weight of plantago and from 1 to 30 percent by weight of pectin.

2. A process for preparing a gastrointestinal composition which consists of the following steps:
   (a) maintaining plantago husks in an atmosphere of ethylene oxide at 10°–35° C. for 6–12 hours, removing the ethylene oxide, and obtaining plantago husks having acceptably low levels of bacterial contamination;
   (b) mixing 100 parts by weight of said last-named husks with 1.01 to 42.8 parts by weight of pectin, roasting the resulting mixture at 120°–180° C. for 0.5 to 2 hours, cooling the resulting roasted mixture to ambient temperature, grinding said roasted mixture, and obtaining the corresponding gastrointestinal composition containing from 99 to 70 percent by weight of plantago and from 1 to 30 percent by weight of pectin.

3. A gastrointestinal composition prepared in accordance with the procedure of claim 1 containing from 99 to 70 percent by weight of plantago husk and from 1 to 30 percent by weight of pectin.

4. A gastrointestinal composition prepared in accordance with the procedure of claim 2 containing from 99 to 70 percent by weight of plantago husk and from 1 to 30 percent by weight of pectin.

5. A gastrointestinal composition containing from 95 to 80 percent by weight of plantago husk and from 5 to 20 percent by weight of pectin, as claimed in claim 4.

6. A gastrointestinal composition containing from 95 to 80 percent by weight of plantago husk and from 5 to 20 percent by weight of pectin, as claimed in claim 3.

7. A method of reducing the incidence and severity of undesirable side effects of anti-ulcer drugs, which comprises administering to a patient suffering from said undesirable side effects an effective undesirable side effects reducing dose of a gastrointestinal composition as claimed in claim 3.

8. A method of alleviating discomfort occasioned by gastroesophageal reflux, which comprises administering to a patient suffering from said discomfort an effective gastroesophageal reflux discomfort alleviating dose of a gastrointestinal composition as claimed in claim 3.

9. A method of reducing the incidence and severity of undesirable side effects of anti-ulcer drugs, which comprises administering to a patient suffering from said undesirable side effects an effective undesirable side effects reducing dose of a gastrointestinal composition as claimed in claim 4.

10. A method of alleviating discomfort occasioned by gastroesophageal reflux, which comprises administering to a patient suffering from said discomfort an effective gastroesophageal reflux discomfort alleviating dose of a gastrointestinal composition as claimed in claim 4.

* * * * *